United States Patent
Maeda et al.

(10) Patent No.: US 6,861,257 B1
(45) Date of Patent: Mar. 1, 2005

(54) METHODS FOR ISOLATION OF OSTEOCLAST PRECURSOR CELLS AND INDUCING THEIR DIFFERENTIATION INTO OSTEOCLASTS

(75) Inventors: Tomoko Maeda, Osaka (JP); Ryuji Suzuki, Osaka (JP); Takahiro Ochi, Hyogo (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/646,899

(22) PCT Filed: Apr. 6, 1999

(86) PCT No.: PCT/JP99/01803

§ 371 (c)(1),
(2), (4) Date: Oct. 10, 2000

(87) PCT Pub. No.: WO99/53023

PCT Pub. Date: Oct. 21, 1999

(30) Foreign Application Priority Data

Apr. 8, 1998 (JP) ............................................. 10/95962
Jun. 18, 1998 (JP) ........................................... 10/170407

(51) Int. Cl.[7] ............................ C12N 5/06; C12N 5/00; C12N 5/08
(52) U.S. Cl. ........................ 435/377; 435/375; 435/372
(58) Field of Search .............................. 435/377, 375, 435/372

(56) References Cited

U.S. PATENT DOCUMENTS 5,830,682 A * 11/1998 Moore ........................ 435/377
5,879,940 A * 3/1999 Torok-Storb et al. ....... 435/366

FOREIGN PATENT DOCUMENTS

| JP | 6-508987 | 10/1994 |
| JP | 7-503127 | 4/1996 |
| WO | WO 96/07733 | 3/1996 |

OTHER PUBLICATIONS

Purton et al. "Normal human peripheral bood mononuclear cells mobilized with granulocyte colony–stimulating factor have increased osteoclastogenic potential compared to non-mobilized blood". Blood. vol. 87, No. 5 (Mar. 1), 1996, pp. 1802–1808.*

Purton et al. Blood, (1995) vol. 86, No. 10 Suppl. 1, p. 488A.*

Matayoshi et al. Proc. Natl. Acad. Sci. USA. Cell Biology. Oct. 1996, vol. 93, pp. 10785–10790.*

Lorenzo et al. Endocrinology. 1987. 121: 1164–1170.*

Kitaura et al. The Journal of Biological Chemistry. 1996. vol. 271, No. 13, pp. 7725–7730.*

Forssmann et al. J. Exp. Med. Jun. 1997, vol. 185, No. 12, pp. 2171–2176.*

Dahl et al. Annals of the Rheumaic Diseases. 1985. 44, 647–657.*

Onoe et al. The Journal of Immunology. 1996. 156: 758–764.*

Tamura Tatsuya et al., "Soluble interleukin-6 receptor triggers osteoclast formation by interleukin 6", Proc. Natl. Acad. Sci. USA, vol. 90 (24) (1993), pp. 11924–11928.

* cited by examiner

*Primary Examiner*—Vera Afremova
(74) *Attorney, Agent, or Firm*—Oblon, Spivak, McClelland, Maier & Neustadt, P.C.

(57) ABSTRACT

This invention relates to: a method for differentiating osteoclast precursor cells (preosteoclasts) into osteoclasts, which comprises culturing the preosteoclasts in the absence of accessory cells; a method for isolating preosteoclasts, which comprises culturing peripheral blood or joint fluid in the absence of cytokine for 1 to 3 weeks; an preosteoclasts, which is obtainable by the above method; a method for differentiating the preosteoclasts obtained by the above method into osteoclasts, which comprises culturing the preosteoclasts in the absence of accessory cell; an osteoclast, which is obtainable by the above method; a method for screening agents for treating metabolic bone diseases, which comprises using the preosteoclasts or the osteoclasts as described above; and agents for treating metabolic bone diseases, which is obtainable by the above screening method.

16 Claims, 5 Drawing Sheets

Figure 1
May-Giemsa stain
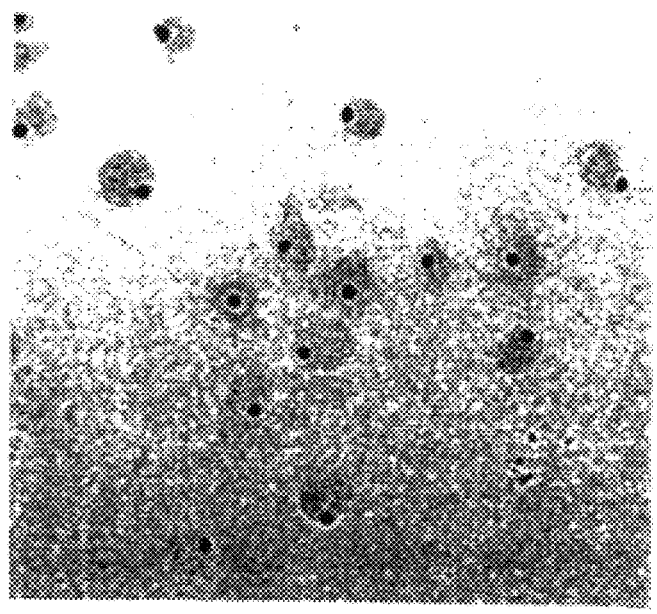
Preosteoclast (×40)
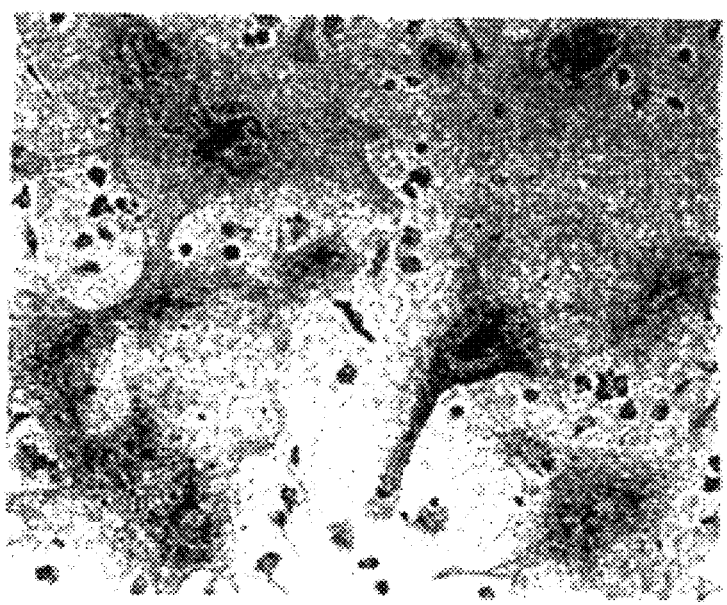
Osteoclast (×20)

Figure 2
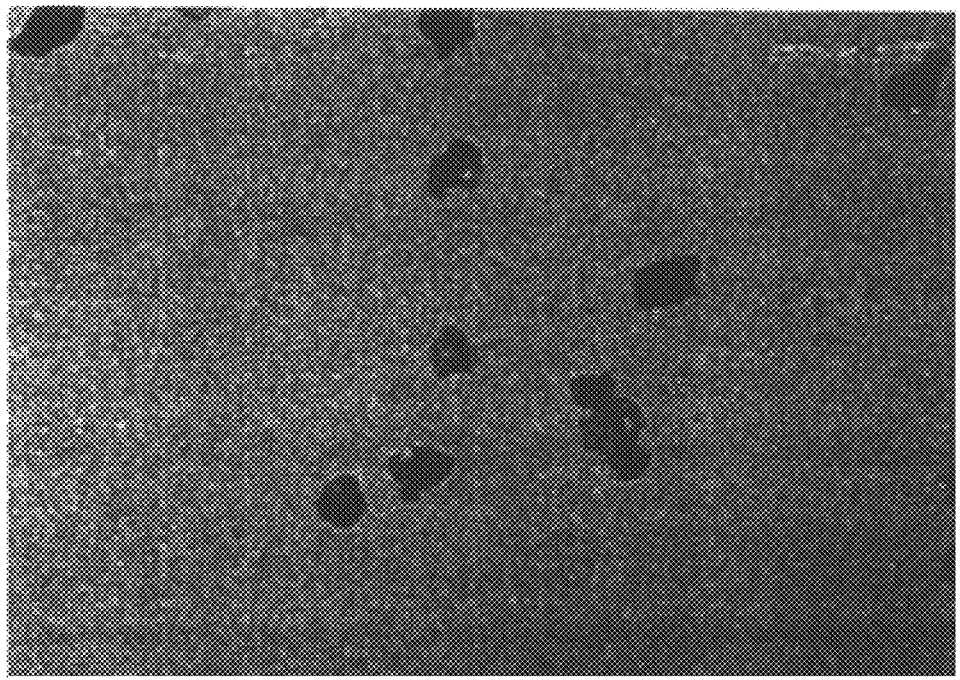
Preosteoclast
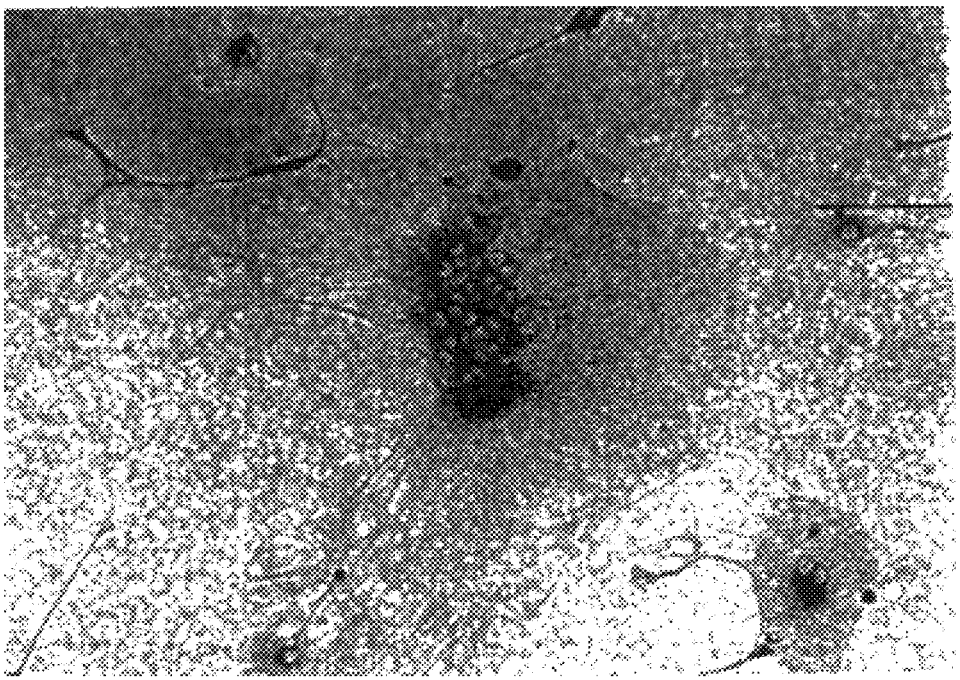
Osteoclast

Figure 3
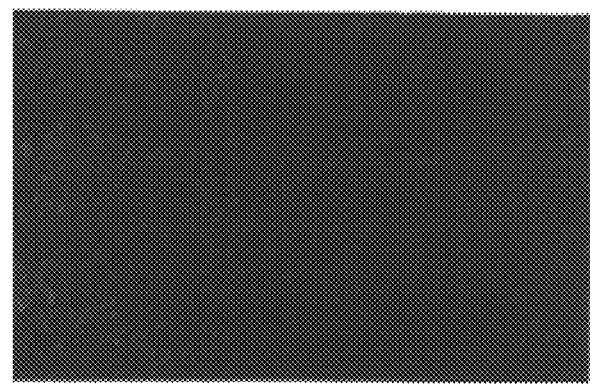
Preosteoclast
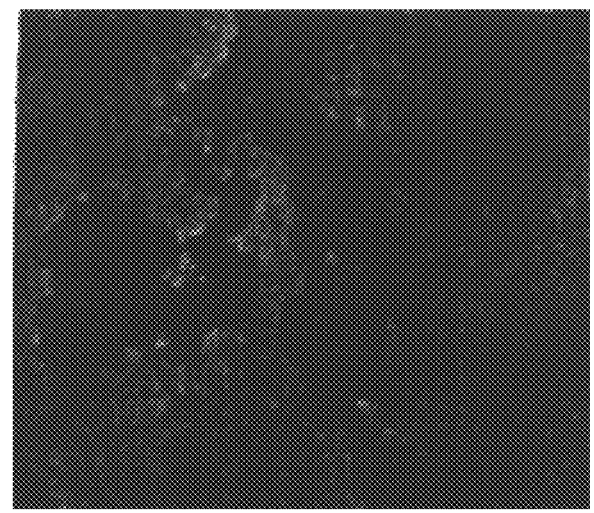
Osteoclast

Figure 6
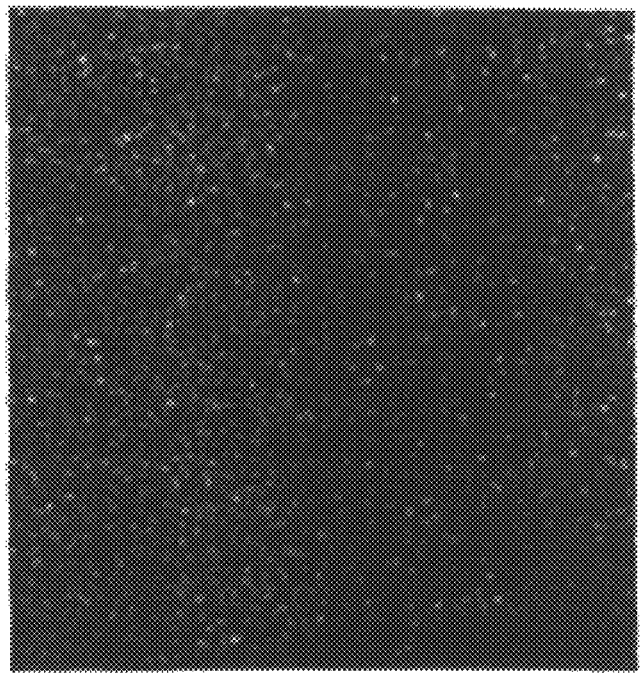
Preosteoclast
Osteoclast

SEQUENCE LISTING

<160> NUMBER OF SEQ ID NOS: 2

<210> SEQ ID NO 1
<211> LENGTH: 467
<212> TYPE: DNA
<213> ORGANISM: Homo sapiens
<220> FEATURE:
<221> NAME/KEY: CDS
<222> LOCATION: (28)..(309)
<223> OTHER INFORMATION:

<400> SEQUENCE: 1

-continued

```
cctgagaagg gcctgatttg cagcatc atg atg ggc ctc tcc ttg gcc tct gct      54
                              Met Met Gly Leu Ser Leu Ala Ser Ala
                               1               5 gtg ctc ctg gcc tcc ctc ctg agt ctc cac ctt gga act gcc aca cgt       102
Val Leu Leu Ala Ser Leu Leu Ser Leu His Leu Gly Thr Ala Thr Arg
10              15                  20                  25 ggg agt gac ata tcc aag acc tgc tgc ttc caa tac agc cac aag ccc       150
Gly Ser Asp Ile Ser Lys Thr Cys Cys Phe Gln Tyr Ser His Lys Pro
                30                  35                  40 ctt ccc tgg acc tgg gtg cga agc tat gaa ttc acc agt aac agc tgc       198
Leu Pro Trp Thr Trp Val Arg Ser Tyr Glu Phe Thr Ser Asn Ser Cys
            45                  50                  55 tcc cag cgg gct gtg ata ttc act acc aaa aga ggc aag aaa gtc tgt       246
Ser Gln Arg Ala Val Ile Phe Thr Thr Lys Arg Gly Lys Lys Val Cys
        60                  65                  70 acc cat cca agg aaa aaa tgg gtg caa aaa tac att tct tta ctg aaa       294
Thr His Pro Arg Lys Lys Trp Val Gln Lys Tyr Ile Ser Leu Leu Lys
    75                  80                  85 act ccg aaa caa ttg tgactcagct gaattgtcat ccgaggacgc ttggaccccg       349
Thr Pro Lys Gln Leu
90 ctcttggctc tgcagccctc tggggagcct gcggaatctt ttctgaaggc tacatggacc    409 cgctggggag gagagggtgt ttcctcccag agttacttta ataaaggttg ttcatagt      467

<210> SEQ ID NO 2
<211> LENGTH: 94
<212> TYPE: PRT
<213> ORGANISM: Homo sapiens

<400> SEQUENCE: 2

Met Met Gly Leu Ser Leu Ala Ser Ala Val Leu Leu Ala Ser Leu Leu
1               5                   10                  15

Ser Leu His Leu Gly Thr Ala Thr Arg Gly Ser Asp Ile Ser Lys Thr
                20                  25                  30

Cys Cys Phe Gln Tyr Ser His Lys Pro Leu Pro Trp Thr Trp Val Arg
            35                  40                  45

Ser Tyr Glu Phe Thr Ser Asn Ser Cys Ser Gln Arg Ala Val Ile Phe
        50                  55                  60

Thr Thr Lys Arg Gly Lys Lys Val Cys Thr His Pro Arg Lys Lys Trp
65                  70                  75                  80

Val Gln Lys Tyr Ile Ser Leu Leu Lys Thr Pro Lys Gln Leu
                85                  90
```

METHODS FOR ISOLATION OF OSTEOCLAST PRECURSOR CELLS AND INDUCING THEIR DIFFERENTIATION INTO OSTEOCLASTS

TECHNICAL FIELD

The present invention relates to a method for the differentiation of osteoclast precursor cells (preosteoclasts) into osteoclasts, which comprises culturing the preosteoclasts in the absence of accesory cells; a method for isolating preosleoclasts; a method for screening agents for metabolic bone diseases, which comprises using the preosteoclasts or the osteoclasts; and agents for metabolic bone diseases, which is obtainable by the screening method.

BACKGROUND ART

Bone tissues of mammal repeat generation and resorption of bone. The tissue operates as a central point of calcium metabolism to keep the balance between bone resorption and generation in the growth period and even after the period of maturity. Bone resorption and resorption are well balanced by crosstalk between osteoclasts and osteoblasts. However, unbalance between bone resorption and generation lead metabolic bone diseases, including osteoporosis, rheumatoid arthritis, osteoarthritis, decrease of bone quantity due to diabetes, many types of hormone abnormalities, nutritional disorder, osteopetrosis and osteomalacia. Cellular pathogenesis of the most of above disorders remain to be elucidated. To resolve the issue and discover therapeutic agents for the metabolic bone diseases, methods for isolation and characterization of osteoclasts and osteoblasts have been required.

It has been studied well for isolation of osteoclasts of mice or rats. Recentry, Fujisawa et al. reported that human osteoclasts were obtained from patients with rheumatoid arthritis (Annals of Rheumatic Diseases. 55;816–822, (1996)). In their study, human osteoclasts were obtained in the presence of a mouse osteoblasts-like cell line, since it has been believed that the presence of accessory cells, such as osteoblasts or bone marrow stromal cells, were indispensable for differentiation of preosteoclasts in vitro. The accessory cells have been believed to play important role for osteoclastogenesisi by close contact with preosteoclasts.

On the other hand, JP 7-194373 describes a method for the differentiation of bone mallow cells into osteoblasts, osteoclasts or chondrocytes in a medium without bone mallow stromal cells or osteoblasts. But, they did not succeed in the isolation of osteoclasts itself. Under the circumstances above, in order to elucidate the mechanism of differentiation of preosteoclasts into osteoclasts, it was required to establish a method for isolation of preosteoclasts, and that for inducing the differentiation into osteoclasts, which needs few factors for the differentiation, and particularly, especially in the absence of accessory cells.

DISCLOSURE OF INVENTION

As a result of intensive studies on the induction of osteoclastgenesis, the present inventors have accomplished inventions on a method for differentiating preosteoclasts into osteoclasts which comprises culturing the osteoclast precursor cells in the absence of accessory cell, a method for isolating preosteoclasts, a preosteoclast which is isolated by the isolating method, a method for differentiating the preosteoclasts isolated by the isolating method into osteoclasts, a osteoclast which is obtainable by the differentiating method, a method for screening agents for metabolic bone diseases and an agent for metabolic bone diseases which is obtainable by the screening method.

The invention relates to:

①  A method for differentiating preosteoclasts into osteoclasts, which comprises culturing the preosteoclasts in the absence of accessory cells;

②  The method as described in ①, which uses a culture medium containing IL-3, IL-7, GM-CSF, eotaxin, eotaxin-2, eotaxin-3 or a mixture of two or more of them;

③  The method as described in ① or ②, which uses a culture medium containing a culture supernatant of mitogen-stimulated peripheral blood mononuclear cells;

④  The method as described in ③, wherein the culture supernatant of mitogen-stimulated peripheral blood mononuclear cells is a culture supernatant of phytohemagglutinin-stimulated human peripheral blood mononuclear cells;

⑤  A method for isolating preosteoclasts, which comprises culturing peripheral blood or joint fluid in the absence of cytokine for 1 to 3 weeks;

⑥  The method as described in ⑤, in which the preosteoslasts are isolated by adding peripheral blood or joint fluid to essential medium for mammalian cells in the absence of cytokine and culturing them at 35–37° C. in 5–7% $CO_2$-containing air for 1–3 weeks to perish cells except preosteoclasts;

⑦  An preosteoclast, which is obtainable by the method described in ⑤ or ⑥;

⑧  A method for differentiating preosteoclasts obtained by the method as described in ⑤ or ⑥ into osteoclasts, which comprises culturing the preosteoclasts in the absence of accessory cells;

⑨  The method as described in ⑧, which uses a culture medium containing IL-3, IL-7, GM-CSF, eotaxin, eotaxin-2, eotaxin-3 or a mixture of two or more of them;

⑩  The method as described in ⑧ or ⑨, which uses a culture medium containing a culture supernatant of mitogen-stimulated peripheral blood mononuclear cells;

⑪  The method as described in ⑩, wherein the culture supernatant of mitogen-stimulated peripheral blood mononuclear cells is a culture supernatant of phytohemagglutinin-stimulated human peripheral blood mononuclear cells;

⑫  An osteoclast, which is obtainable by the method as described in any one of ① to ④ and ⑧ to ⑪;

⑬  A method for screening agents for metabolic bone diseases, which comprises using the preosteoclasts isolated by the method as described in ⑤ or ⑥;

⑭  A method for screening agents for metabolic bone diseases, which comprises using the preosteoclasts as described in ⑦;

⑮  A method for screening agents for metabolic bone diseases, which comprises using the osteoclasts obtained by the method as described in any one of ① to ④ and ⑧ to ⑪.

⑯  A method for screening agents for metabolic bone diseases, which comprises using the osteoclasts as described in ⑫;

⑰  An agent for metabolic bone diseases, which is obtainable by the method as described in any one of ⑬ to ⑯.

One of the invention relates to a method for differentiating preosteoclasts into osteoclasts, which comprises culturing the preosteoclasts in the absence of accessory cell. In this case, "accessory cell" means mesenchymal cell which can induce the differentiation of preosteoclasts by producing adhesive factors and soluble factors. As a "accessory cell", bone mallow stromal cells, osteoblasts (osteoblast like cells), fibroblasts and tumor cells are given for examples. "Osteoclast precursor cells" or "Preosteoclasts" means cells which do not substantially contain any admixture cell. Concretely, it means human preosteoclasts. "Osteoclast precursor cells" or "Preosteoclasts" also means hematopoietic stem cell-derived cells which have an ability of differentiating into osteoclasts under an appropriate culture condition. "Osteoclasts" means cells which do not substantially contain any admixture cells. Concretely, it means human osteoclasts. "Osteoclasts" also means cells which are multinucleate (N>3), positive for tartrate-resistant acid phosphatase, and have an ability of bone resorption.

Further, this invention relates to a method for differentiating preosteoclasts into osteoclasts, which uses a culture medium containing IL-3, IL-7, GM-CSF, eotaxin (Kitaura, M. et al., J. Biol. Chem., 271, 13, 7725–7730, 1996), eotaxin-2 (Forssmann, U. et al., J. Exp. Med., 185, 12, 2171–2176, 1997), eotaxin-3 (human CC type chemokine. The nucleic acid sequence is shown at SEQ ID No.:1, and the amino acid sequence is shown at SEQ ID No.:2) or a mixture of two or more of them. IL-3, IL-7, GM-CSF, eotaxin, eotaxin-2 and eotaxin-3, each may be natural type or recombinant type. As the culture medium which contains IL-3, IL-7, GM-CSF, eotaxin, eotaxin-2, eotaxin-3 or a mixture of two or more of them, a culture supernatant of mitogen-stimulated peripheral blood mononuclear cells can be used. As the culture supernatant of mitogen-stimulated peripheral blood mononuclear cells, a culture supernatant of phytohemagglutinin-stimulated human peripheral blood mononuclear cells can be used.

The invention also relates to a method for isolating preosteoclasts by culturing peripheral blood or joint fluid in the absence of cytokine for 1 to 3 weeks. In detail, the invention relates to a method for isolating preosteoslasts by adding peripheral blood or joint fluid to essential medium for mammalian cells in the absence of cytokine, and culturing them at 35–37° C., in 5–7% $CO_2$-containing air for 1–3 weeks to perish cells except preosteoclasts. Further, the invention relates to preosteoclasts which are obtainable by the method.

"Peripheral blood" means mammalian peripheral blood, concretely, human peripheral blood. As the peripheral blood, peripheral blood of healthy donors subjects can be used.

As "joint fluid", not only joint fluid of healthy donors but also joint fluid of rheumatoid arthritis (RA) subjects can be used.

"Essential medium for Mammalian cells" means an isotonic buffer solution which contains inorganic salts, essential amino acids or its derivatives, and vitamin and its derivatives, which are available for cells to survive. As the "essential medium for mammalian cells", Dulbecco's Modified Eagle Medium(DMEM), RPMI1640 and AIM-V are given for examples.

Further, the invention relate to a method for differentiating preosteoclasts into osteoclasts, which comprises culturing in the absence of accessory cell the preosteoclasts which are isolated by culturing the peripheral blood or joint fluid as described previously in the absence of cytokine for 1 to 3 weeks. Concretely, the invention relates to a method for differentiating preosteoclasts into osteoclasts, which uses a culture medium containing IL-3, IL-7, GM-CSF, eotaxin, eotaxin-2, eotaxin-3 or a mixture of two or more of them. As IL-3, IL-7, GM-CSF, eotaxin, eotaxin-2 or eotaxin-3, each may be natural type or recombinant type. As a culture medium which contains IL-3, IL-7, GM-CSF, eotaxin, eotaxin-2, eotaxin-3 or a mixture consisted by a combination of two or more of them, a culture supernatant of mitogen-stimulated peripheral blood mononuclear cells is available. As a culture supernatant of mitogen stimulated peripheral blood mononuclear cells, a culture supernatant of phytohemagglutinin stimulated human peripheral blood mononuclear cells is available.

As another embodiment, the invention relates to a method for screening agents for metabolic bone diseases, which comprises using the preosteoclasts or the osteoclasts of this invention, and to an agent for metabolic bone diseases which is obtainable by the screening method. As the "metabolic bone disease", osteoporosis, rheumatoid arthritis, decrease of bone quantity due to diabetes, osteomalacia, and osteopetrosis are given for example.

As "a method for screening agents for metabolic bone diseases", (1) a method for measuring inhibitory activities on the differentiation of preosteoclasts into osteoclasts, and (2) a method for measuring inhibitory activities on the bone resorption by osteoclasts are given for example. If a candidate compound for the therapeutic agent shows a differentiation inhibitory activity against the preosteoclasts of this invention, the compound is promising as an antirheumatic drug. Futher, if a candidate compound for the therapeutic agent shows a bone resorption inhibitory activity against the osteoclasts of this invention, it is suggested that the compound is useful for treating osteoporosis caused by excessive bone resorption, decrease of bone mass due to diabetes, osteomalacia or the like. Thus, by using the preosteoclasts or the osteoclasts of this invention, the screening for bone metabolic diseases agents can easily be performed in vitro.

BRIEF DESCRIPTION OF DRAWINGS

FIG. 1 is photomicrographs which show that the preosteoclasts and the osteoclasts stained by May-Giemsa solution.

FIG. 2 is photomicrographs which show that the TRAP activities in the preosteoclasts and the osteoclasts.

FIG. 3 is photomicrographs which show the resorption activities of the preosteoclasts and the otsteoclasts, which was tested by using dentine slices.

FIG. 6 is photomicrographs which show the resorption activities of the preosteoclasts and the otsteoclasts, which was tested by using a hydroxyappatite sintering quartz disc.

BEST MODE FOR CARRYING OUT THE INVENTION

Figure 4:
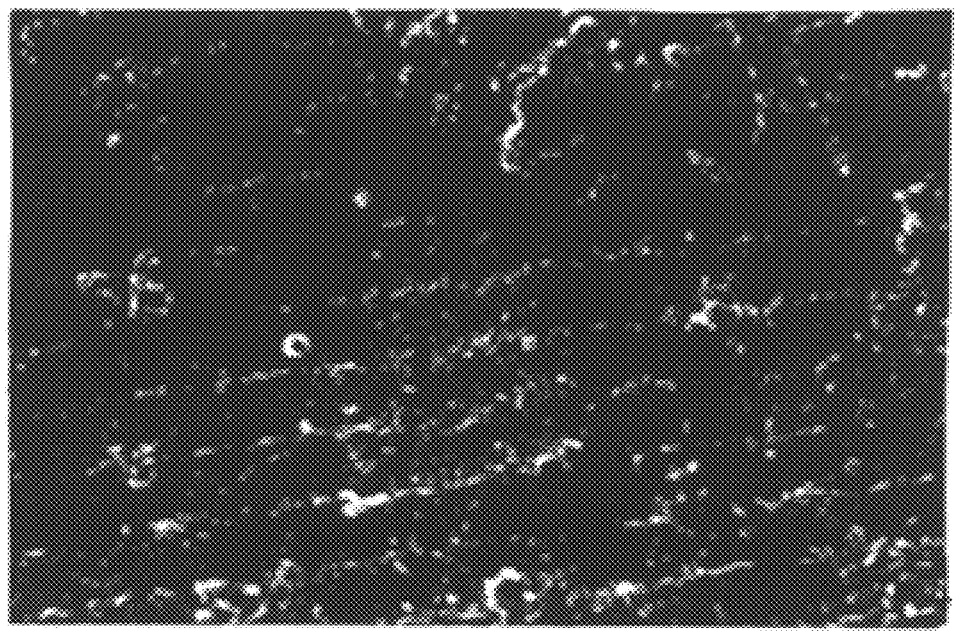
FIG. 4 is a photomicrograph which shows resorption pits on dentine slice formed by the osteoclasts.

The human osteoclasts of the invention can be obtained by the following methods.

Isolation of Preosteoclasts

Isolation of osteoclast precursor cells comprises (1) separation step of cellular fraction and (2) isolation step of preosteoclasts.

(1) Separation of Cellular Fraction

Preotsteolasts can be obtained from peripheral blood of healthy donors or joint fluid of rheumatoid arthritis subjects. The volume of bodily fluids necessary for isolating the cells is 50 ml to 200 ml for peripheral blood of normal subjects, or 1 ml to several tens ml for joint fluid of rheumatoid arthritis subjects. In the case of using peripheral blood of healthy donors, the blood is collected in the presence of heparin or an alternative anticoagulant. Peripheral blood mononuclear cells (PBMC) are obtained from the blood by excluding of erythrocyte using a specific gravity centrifugation or ammonium chloride so on.

On the other hand, in the case of using joint fluid of rheumatoid arthritis subjects, the cellular fraction can be obtained by the centrifugation of the joint fluid, if necessary by adding essential medium for mammalian cells, such as RPMI1640, thereto.

(2) Isolation of Preosteoclasts

The obtained cellular fraction is cultured in essential medium for mammalian cells, such as DMEM, at 35–37° C., preferably, 37° C., for several weeks, preferably, 1–3 weeks, in 5–7% $CO_2$-containing air. This culture make cells except preosteoclasts perish, and the preosteoclasts can be isolated.

Isolation of Osteoclasts

Isolation of osteoclasts comprises (1) preparation step of culture medium and (2) differentiation-inducing step of preosteoclasts into osteoclasts.

(1) Preparation of Culture Medium

The medium is prepared by an addition of cytokines to essential medium for mammalian cells, such as AIM-V to induce the differentiation. Preferably, antibiotics are added to the medium for preventing the contamination of bacteria. According to the invention, IL-3, IL-7, GM-CSF, eotaxin, eotaxin-2, eotaxin-3 are given for example as the cytokine which have an activity to induce the differentiation of the preosteoclasts. These cytokines may be added as alone or mixture thereof.

(2) Differentiation Induction of Preosteoclasts into Osteoclasts

The obtained preosteoclsats are cultured at 35–37° C., for 48–96 hours in the medium described above. The preosteoclasts are differentiated into osteoclasts by the stimulation of the cytokines described above. Thus, the osteoclasts can be isolated.

Screening of Therapeutic Agents for Metabolic Bone Diseases

As a method for screening therapeutic agents for metabolic bone diseases, (1) a method for measuring inhibitory activities on the differentiation of preosteoclasts into osteoclasts, and (2) a method for measuring inhibitory activities on bone resorption by the osteoclasts are given for example.

(1) Measuring Method of Differentiation Inhibitory Activity

For example, the preosteoclasts obtained by the invention are prepared as $1 \times 10^6$ cell/well and cultured on 48 wells plate. In the cultivation, essential medium for mammalian cells, contains IL-3, IL-7, GM-CSF, eotaxin, eotaxin-2, eotaxin-3 or a supernatant of mitogen-stimulated peripheral blood mononuclear cells, is used. Various concentration of a candidate compound for therapeutic agents is added into the each well, and the prepared plate is cultured at 37° C., for 48–96 hours. At the end of the culture period, the adherent cells are fixed and stained with tartrate-resistant acid phosphatase (TRAP) which is the specific maker enzyme for osteoclasts. The multinucleate (N>3) and TRAP positive cell is counted as an osteoclast in each well. By calculating the result as $IC_{50}$, it is possible to evaluate the differentiation inhibitory activity of the candidate compound against the preosteoclasts.

(2) Measuring Method of Bone Resorption Inhibitory Activity

For example, the osteoclasts obtained by the invention are prepared as $1 \times 10^6$ cell/well and cultured on a dentine slice in the essential medium for mammalian cells 48-well culture plate. Various concentration of a candidate compound for therapeutic agents is added into the each well, and the cells are cultured at 37° C., for 48–96 hours. At the end of the culture period, the dentine slice is stained with hematoxylin. Osteoclasts resorb hydroxyappatite, and the resorbed parts (resorption pit) is visualized by the hematoxylin staining when the bone resorption is occurred. The formation of resorption pit on dentine slice is observed microscopically or an electron-microscopically. Otherwise, the change of calcium concentration in the culture supernatant can be assayed. By calculating the result as $IC_{50}$, it is possible to evaluate a bone resorption inhibitory activity of the candidate compound against the osteoclasts.

The inhibitory activity on the osteoclasts formation is becoming important as an indicator for assessing an antirheumatic activity. Consequently, a compound which has a differentiation inhibitory activity against preosteoclasts, is hopeful as an antirheumatic drug. Further, osteoporosis is caused by an excessive bone resorption. Thus, a compound with a bone resorption inhibitory activity against osteoclasts is hopeful as a therapeutic agent for osteoporosis.

EXAMPLE

Example 1

Isolation of Human Osteoclasts from Joint Fluid of Patients with Rheumatoid Arthritis (1) Separation of a Cellular Fraction Joint fluids were obtained from patients with rheumatoid arthritis. The joint fluids were kept in tubes at 4° C. The following procedures were generally under sterile conditions. The joint fluid, 1 ml to several tens ml, was added to equal volume of RPMI 1640 medium (Gibco BRL, #22400 or equivalent). The mixture was centrifugated at 1,000–2,000 rpm for 5 minutes at 4° C. to obtain a cellular fraction containing granulocytes and lymphocytes.

(2) Isolation of Preosteoclasts

The obtained cellular fraction was cultured in DMEM medium (Gibco BRL, #12430-21 or equivalent) supplemented with 10% (v/v) of fetal calf serum (FCS) in 5–7% $CO_2$-containing air at 37° C. for several weeks. During the culture period, all cells except preosteoclasts died out, and only preosteoclasts survived (FIGS. 1, 2).

(3) Preparation of Medium

The medium was prepared for the differentiation of preosteoclasts into osteiclasts . Four hundred ml of 400 ml of AIM-V medium (Gibco BRL, #87-0112) was supplemented with 60 ml of RPMI1640 medium (Gibco BRL, #22400), 40 ml of human T-STIM (10 BRMP/ml; BRMP, Biological Response Modifier Program Jurkat IL-2 reference reagent), 50 ml of 10% FCS (inactivated in advance by heating at 56° C. for 30 minutes), and antibiotics (100 U of penicillin and 100 μg/ml of streptomycin; Gibco BRL, #15140-015 or equivalent), and used as Medium A. Human T-STIM is a culture supernatant of human peripheral blood mononuclear cells stimulated with phytohemagglutinin (Human T-STIM with PHA, Becton Dickinson, #40045).

(4) Induction of Differentiation of Preosteoclasts Into Osteoclasts

The preosteoclasts obtained in Example 1(2) were stimulated with Medium A described in Example 1(3) at 37° C. for 48–96 hours. In the culture condition, the differentiation of preosteoclasts into osteoclasts was observed (FIG. 1, 2).

(5) Identification of the Cytokine Possesing a Differentiation-inducing Ability

Human T-STIM contains a variety of cytokines. In order to identify the cytokine which stimulates differentiation of preosteoclasts into osteoclasts, the differentiation was examined by modifycation the contents of Medium A described as previously in Example 1(3).

① Preparation of the Medium

The following 16 kinds of medium (B-R) were prepared by using the cytokines shown below, alone or a mixture thereof, instead of human T-STIM contained in Medium A (Example 1(3)). The other materials than human T-STIM, namely, AIM-V medium, RPMI 1640 medium, 10% FCS and antibiotics (100 U of penicillin and 100 $\mu$g/ml of streptomycin; Gibco BRL, #15140-015 or it's equivalent) were the same as those contained in Medium A.

Medium B: 0.5–5 ng/ml of recombinant human IL-1 (R & D Systems, #201-LB, #200-LA or equivalent)+400 ml of AIM-V medium+60 ml of RPMI 1640 medium+50 ml of FCS+antibiotics Medium C: 50–200 U/ml of recombinant human IL-2 (R & D Systems, #202-IL, or equivalent)+400 ml of AIM-V medium+60 ml of RPMI 1640 medium+50 ml of FCS+antibiotics Medium D: 2–10 ng/ml of recombinant human IL-3 (R & D Systems, #403-ML-010 or equivalent)+400 ml of AIM-V medium+60 ml of RPMI 1640 medium+50 ml of FCS+antibiotics Medium E: 50–200 U/ml of recombinant human IL-4 (Genzyme, #2181-01 or equivalent)+400 ml of AIM-V medium+60 ml of RPMI 1640 medium+50 ml of FCS+antibiotics Medium F: 10–20 ng/ml of recombinant human IL-6 (R & D Systems, #206-IL or equivalent)+400 ml of AIM-V medium+60 ml of RPMI 1640 medium+50 ml of FCS+antibiotics Medium G: 10–20 ng/ml of recombinant human IL-6 (R & D Systems, #206-IL or equivalent)+100–300 ng/ml of recombinant human soluble IL-6 receptor (R & D Systems, #227-SR or it's equivalent)+400 ml of AIM-V medium+60 ml of RPMI 1640 medium+50 ml of FCS+antibiotics Medium H: 5–20 ng/ml of recombinant human IL-7 (Genzyme, #1587-00 or equivalent)+400 ml of AIM-V medium+60 ml of RPMI 1640 medium+50 ml of FCS+antibiotics Medium I: 1–4 ng/ml of recombinant human IL-11 (R & D Systems, #218-IL or equivalent)+400 ml of AIM-V medium+60 ml of RPMI 1640 medium+50 ml of FCS+antibiotics Medium J: 2.5–100 ng/ml of recombinant human M-CSF (R & D Systems, #216-MC-010 or equivalent)+400 ml of AIM-V medium+60 ml of RPMI 1640 medium+50 ml of FCS+antibiotics Medium K: 1–5 ng/ml of recombinant human GM-CSG (R & D Systems, #215-GM-010 or equivalent)+400 ml of AIM-V medium+60 ml of RPMI 1640 medium+50 ml of FCS+antibiotics Medium L: 2–10 ng/ml of recombinant human IL-3 (R & D Systems, #403-010 or equivalent)+5–20 ng/ml of recombinant human IL-7 (Genzyme, #1587-00 or it's equivalent)+400 ml of AIM-V medium+60 ml of RPMI 1640 medium+50 ml of FCS+antibiotics Medium M: 5–20 ng/ml of recombinant human IL-7 (Genzyme, #1587-00 or equivalent)+1–5 ng/ml of recombinant human GM-CSF (R & D Systems, #215-GM-010 or equivalent)+400 ml of AIM-V medium+60 ml of RPMI 1640 medium+50 ml of FCS+antibiotics Medium N: 2–10 ng/ml of recombinant human IL-3 (R & D Systems, #403-ML-010 or equivalent)+5–20 ng/ml of recombinant human IL-7 (Genzyme, #1587-00 or equivalent)+1–5 ng/ml of recombinant human GM-CSF (R & D Systems, #215-GM-010 or equivalent)+400 ml of AIM-V medium+60 ml of RPMI 1640 medium+50 ml of FCS+antibiotics Medium P: 10–1000 ng/ml of recombinant human eotaxin (R & D Systems, #220-EO or equivalent)+400 ml of AIM-V medium+60 ml of RPMI 1640 medium+50 ml of FCS+antibiotics Medium Q: 10–1000 ng/ml of recombinant human eotaxin-2 (R & D Systems, #343-E2 or equivalent)+400 ml of AIM-V medium+60 ml of RPMI 1640 medium+50 ml of FCS+antibiotics Medium R: 10–1000 ng/ml of recombinant human Eotaxin-3+400 ml of AIM-V medium+60 ml of RPMI 1640 medium+50 ml of FCS+antibiotics (Eotaxin-3 was found in the human genome sequencing data (H RG356E01) published by Washington University Genome Sequence Center, an exson sequence, which is considered to exhibit a significant homology but to encode a different chemokine protein, compared to known CC type chemokines. According to the sequence, cDNA of eotaxin-3 was obtained as shown in SEQ ID No.1. Recombinant baculovirus containing the sequence was prepared to infect insect cells, then the recombinant eotaxin-3 protein was purified from the culture supernatant.)

② Induction of the differentiation of preosteoclasts into osteiclasts

The preosteoclasts obtained by Example 1(2) were cultured in the Medium B-N described above at 37° C. for 48–96 hours. The differentiation of preosteoclasts into osteoclats was observed in the Medium D, H, K, M, N, P, Q and R. However, the differentiation was not occurred in the Medium B, C, E, F, G, I and J. From these results, it has become clear that IL-3, IL-7, GM-CSF, eotaxin, eotaxin-2, eotaxin-3 and the mixture thereof have an ability for inducing the differentiation of preosteoclasts. And, it was confirmed that IL-1, IL-2, IL-4, IL-6, IL-11 and M-CSF do not have an ability for inducing the differentiation of preosteoclasts.

On the differentiation requiring the presence of accessory cells, it has been known that IL-1, IL-6, IL-11, and M-CSF induce the differentiation of preosteoclasts into osteoclasts. But it has not been clear that the differentiation was induced by the result of the stimulation of preosteoclasts or accessory cells.

On the other hand, on the differentiation of preosteoclasts in this invention which does not require the presence of accessory cell, it becomes clear that IL-3, IL-7, GM-CSF, eotaxin, eotaxin-2, and eotaxin-3 have the differentiation-inducing ability. Furthermore, IL-1, IL-6, IL-11 or M-CSF does not effect to the differentiation.

Example 2

Isolation of Human Osteoclasts from Peripheral Blood of Healty Donors (1) Separation of Cellular Fraction Fifty ml to 200 ml of peripheral blood of healthy donors were collected in the presence of heparin or an alternative anticoagulant. Peripheral blood mononuclear cells (PBMC)

were obtained by a specific gravity centrifugation using a Ficoll-paque (Pharmacia Biotech). $10^7$ cell/ml of PBMC were suspended in RPMI1640 medium containing 10% (v/v) FCS, then 1–1.5 ml/dish of the cell suspension was cultured on 60 mm culture dish at 37° C., in 5–7% $CO_2$-containing air, for 1–2 hours. After the culture, the non-adherent cells were rinsed out from the dish with RPIM1640 medium containing 10% (v/v) of FCS at 37° C. Adherent cells to the dish were washed with cold (4° C.), serum-free RPIM1640 medium, then the cells were collected as a peripheral blood monocytes (about 3–8% of total PBMC).

(2) Isolation of Preosteoclasts

The obtained monocytes ($0.5-1\times10^6$/ml) was cultured in DMEM medium (Gibco BRL, #12430-21 or equivalent) supplemented with 10% of FCS in 5–7% $CO_2$-containing air at 37° C. for several weeks likewise Example 1 (2). During the culture period, all cells except preosteoclasts died out, and only preostetoclasts survived. In cocultivation of the peripheral blood monoctyes and synovial nurse cells-derived rheumatoid arthritis subjects, the proliferation efficiency of the preosteoclasts increased. At the time, the same medium as Example 1 (2) was used.

(3) Induction of Differentiation

The preosteoclcasts were stimulated with Medium A described in Example 1(3) at 37° C. for 48–96 hours. The differentiation of preosteoclasts was occurred and osteoclasts were obtained.

It was confirmed that the cells obtained at Example 1(4) and Example 2(3) were osteoclasts by the following testing examples.

Testing Example (1) Morphologic Observation

The cells were stained by May-Giemsa solution, and were examined microscopically. The stained preosteoclasts and the stained osteiclasts are shown in FIG. 1 instead of photomicrograph. Form the result, it was confirmed that the preosteoclasts before the differentiation had a monocyte like morphilogy and the osteoclasts were multinucleated (over 3–100) giant cells.

(2) TRAP Stain

The preosteoclasts before the differentiation and the osteoclasts after the differentiation were stained by using a TRAP (tartrate-resistant acid phosphatase) staining kit (Sigma Co.) and examined by a microscope. The cells before the differentiation (preosteoclasts) and the cells after the differentiation (osteoclasts) are shown in FIG. 2 instead of photomicrograph. The figures shows that the cells before the differentiation (preosteoclasts) were positive for TRAP, and the cells after the differentiation (osteoclasts) were positive for TRAP especially around the nuclei.

(3) Bone Resorbing Activity

The preosteoclasts were cultured on dentine slices under the condition which cause the differentiation (Example 1(4)), then the dentine slices were stained with hematoxylin (Sigma Co.) and examined by a microscope. FIG. 3 shows the surfaces of the slice instead of the photomicrograph. The preosteoclasts before the differentiation had no effect on the dentine slices. But the osteoclasts after the differentiation resorbed calcium phosphate and the resorption pit on the slices were strongly stained with the dye. The dentine slices resorbed by the osteoclasts were examined by a scanning electron microscopy. FIG. 4 shows the figure instead of the scanning electron photomicrograph. The formation of the resorption pit is noted at the center of the figure. The resorption of calcium phosphate formed the pit and collagen fibers were exposed outside.

Futher, the preosteoclasts were differentiated on calcium phosphate sintering quartz discs (Osteologic™, Sumisho Pharma) and the discs were examined by a phase-contrast microscope. FIG. 5 shows the figure instead of the phase-contrast photomicrograph. The preosteoclasts before the differentiation had no effect on the calcium phosphate sintering quartz discs. But the resorption (the transparent area of the disc) by the osteoclasts after the differentiation was observed.

From the results shown in the testing examples, it was confirmed that the cells before the differentiation were preosteoclasts and the cells after the differentiation were osteoclasts.

Industrial Applicability

According to the invention, osteoclasts can be obtained from the same individual repeatedly, thus the pathophysiological or immunological investigation of the osteoclasts can be performed by using them. The screening of candidate compounds useful for treating metabolic bone diseases can be examined easily by using the osteoclast precurosor cells or osteoclasts of the invention. For example, it is effective to use a compound, which is obtained by the screening for bone resorption-inhibitory activity against the osteoclasts and shows a bone resorption-inhibiting ability against the osteoclasts, to treat the metabolic bone disease, including osteoporosis caused by an excessive bone resorption, decrease of bone quantity due to diabetes, and osteomalacia.

What is claimed is:

1. A method for producing an osteoclast, comprising:
    culturing an osteoclast precursor cell in the absence of accessory cells in a culture medium comprising one or more compound(s) selected from the group consisting of IL-3, IL-7, GM-CSF, eotaxin, eotaxin-2, and eotaxin-3, or in a culture medium comprising a culture supernatant of mitogen-stimulated peripheral blood mononuclear cells and
    recovering or isolating an osteoclast;
    wherein said osteoclast precursor cell is obtained by culturing a hematopoietic stem cell-derived cell obtained from peripheral blood or joint fluid in an essential medium for mammalian cells, optionally with added serum, in the absence of additional cytokine(s).

2. The method of claim 1, wherein said osteoclast precursor cell is obtained by culturing the cell obtained from joint fluid.

3. The method of claim 1, wherein said osteoclast precursor cell is obtained by culturing the cell obtained from peripheral blood.

4. The method of claim 1, wherein said culture medium comprises IL-3.

5. The method of claim 1, wherein said culture medium comprises IL-7.

6. The method of claim 1, wherein said culture medium comprises GM-CSF.

7. The method of claim 1, wherein said culture medium comprises eotaxin.

8. The method of claim 1, wherein said culture medium comprises eotaxin-2.

9. The method of claim 1, wherein said culture medium comprises eotaxin-3.

10. The method of claim 1, wherein said culture medium comprises a culture supernatant of mitogen-stimulated peripheral blood mononuclear cells.

11. The method of claim 1, wherein said culture supernatant is a culture supernatant of phytohemagglutinin-stimulated human peripheral blood mononuclear cells.

12. The method of claim 1, wherein said osteoclast precursor cell is obtained by culturing said hematopoietic stem cell-derived cell for 1–3 weeks.

13. The method of claim 1, wherein said essential medium for mammalian cells contains serum.

14. The method of claim 1, wherein said hematopoietic stem cell-derived cell is obtained from peripheral blood mononuclear cells.

15. The method of claim 1, wherein said hematopoietic stem cell-derived cell is obtained from a cellular fraction of joint fluid which contains granulocytes and lymphocytes.

16. The method of claim 1, wherein said hematopoietic stem cell-derived cell is cultured at a temperature of 35–37° C. in 5–7% $CO_2$-containing air for 1–3 weeks.

* * * * *